United States Patent

Takemoto et al.

[11] Patent Number: 5,391,809
[45] Date of Patent: Feb. 21, 1995

[54] METHOD FOR THE PRODUCTION OF α-L-ASPARTYL-L-PHENYLALANINE METHYL ESTER HYDROCHLORIDE

[75] Inventors: Tadashi Takemoto, Kawasaki; Shinji Fujita, Yokkaichi, both of Japan

[73] Assignee: Ajinomoto Co., Inc., Tokyo, Japan

[21] Appl. No.: 99,542

[22] Filed: Jul. 30, 1993

[30] Foreign Application Priority Data

Aug. 5, 1992 [JP] Japan .................................. 4-209153

[51] Int. Cl.$^6$ ........................................... C07C 229/18
[52] U.S. Cl. ................................................. 560/41
[58] Field of Search ..................................... 560/41

[56] References Cited

U.S. PATENT DOCUMENTS

| | | | |
|---|---|---|---|
| 4,684,745 | 8/1987 | Takemoto et al. | 560/41 |
| 5,053,532 | 10/1993 | Hill et al. | 560/41 |

FOREIGN PATENT DOCUMENTS

| | | |
|---|---|---|
| 0128694 | 12/1984 | European Pat. Off. . |
| 0187530 | 7/1986 | European Pat. Off. . |
| 0491173 | 6/1992 | European Pat. Off. . |

Primary Examiner—José G. Dees
Assistant Examiner—Joseph M. Conrad, III
Attorney, Agent, or Firm—Oblon, Spivak, McClelland, Maier, Neustadt

[57] ABSTRACT

A method is disclosed for the production of α-APM.HCl by treating an F-α-AP derivative with a mixed solvent of methanol, hydrochloric acid and water, wherein the solubility of α-APM.HCl is lowered to increase the separation yield thereof.

9 Claims, 1 Drawing Sheet

METHOD FOR THE PRODUCTION OF α-L-ASPARTYL-L-PHENYLALANINE METHYL ESTER HYDROCHLORIDE

DETAILED DESCRIPTION OF THE INVENTION

1. Field of the Invention

The present invention relates to a method of obtaining α-L-aspartyl-L-phenylalanine methyl ester in the form of a hydrochloride (α-APM.HCl), which is a peptide sweetener capable of providing a sweetness of approximately 200 times that of sucrose, and which is in high demand as a dietary sweetener due to its high quality of sweetness and low calorie content.

2. Discussion of the Background

Various methods for the production of α-APM.HCl are known, and representative examples thereof from the point of view of industrial production include a method wherein N-formyl-α-L-aspartyl-L-phenylalanine methyl ester (F-α-APM) is treated with methanol and highly concentrated hydrochloric acid (U.S. Pat. No. 4,684,745) and a method wherein N-formyl-α-L-aspartyl-L-phenylalanine (F-α-AP) is esterified using methanol, hydrochloric acid and water (U.S. Pat. No. 3,933,781).

These methods are industrially useful for the production of α-APM.HCl; however, these methods require the precipitation of α-APM.HCl from the reaction mixture. Unfortunately, a substantial amount of the α-APM.HCl remains in the separated mother liquor after precipitation. It is therefore desirable to lower the solubility of α-APM.HCl so as to increase the yield of α-APM.HCl.

SUMMARY OF THE INVENTION

Accordingly, one object of this invention is to provide a method for the industrial production of α-APM.HCl, wherein the solubility of α-APM.HCl is lowered so as to increase the separation of α-APM.HCl for the reaction mixture.

Figure 1:
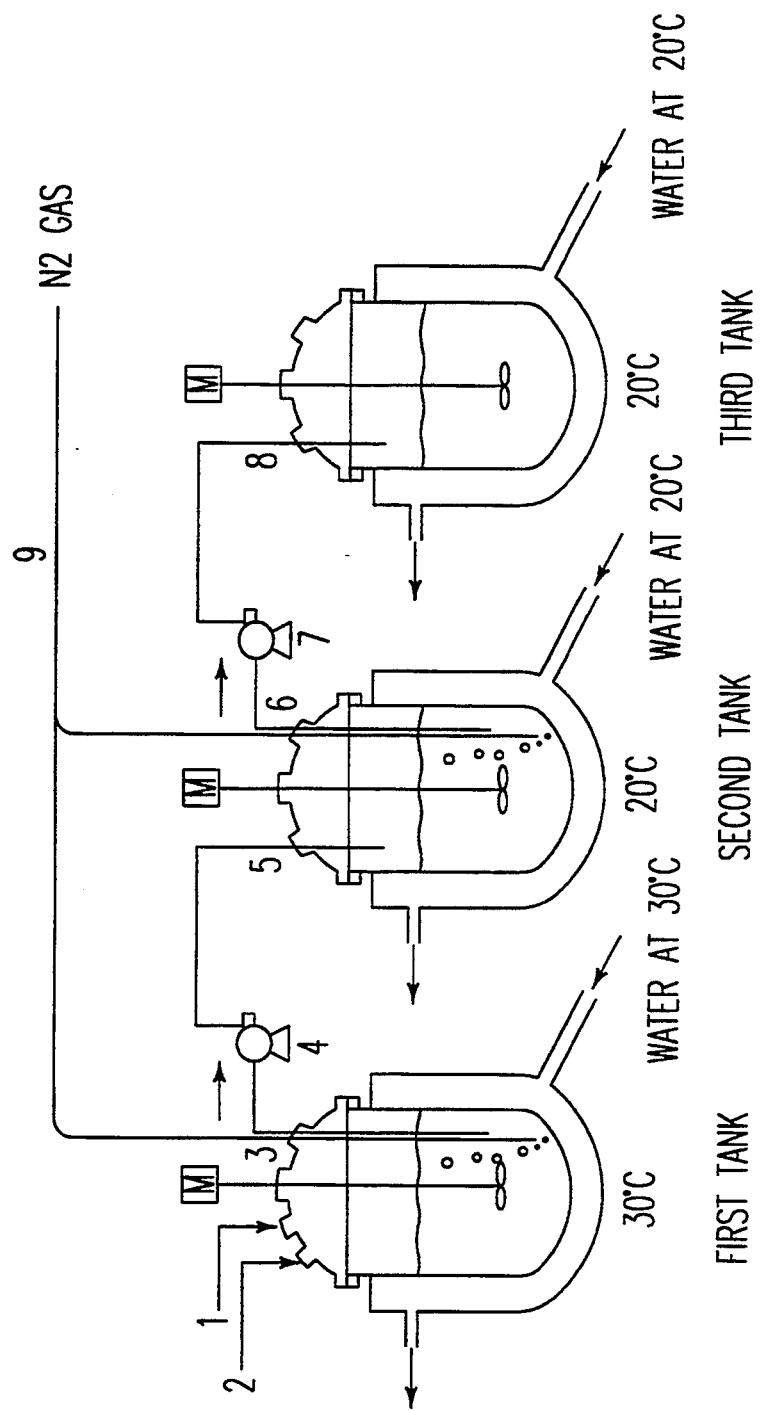
FIG. 1

An overview of the apparatus used in the production of α-APM.HCl as described in Example 6.

DETAILED DESCRIPTION OF THE PREFERRED EMBODIMENTS

Accordingly, the present invention provides a method for the production of α-APM by treating an F-α-AP derivative with a mixed solvent of methanol, hydrochloric acid and water, wherein the treatment is performed in the presence of an inert gas or wherein the treatment is effected under reduced pressure.

F-α-AP derivatives, useful as starting materials in the process of the present invention, can be industrially produced using conventional methods. For example, F-α-APM can be produced by condensing N-formyl-L-aspartic anhydride and L-phenylalanine methyl ester in a mixed solvent of toluene and acetic acid. Following the reaction, acetic acid is removed, water is added, and F-α-APM is extracted into the water layer to obtain an aqueous solution of F-α-APM (Japanese Patent Application HEI 3-221332). F-α-AP can be produced by condensing N-formyl-L-aspartic anhydride and L-phenylalanine in a mixed solvent of acetic acid and an ester of acetic acid (U.S. Pat. No. 4,946,988).

Suitable methods in accordance with the present invention for obtaining α-APM.HCl by treating an F-α-AP derivative with a mixed solvent of methanol, hydrochloric acid and water include:

1) Suspending or dissolving an F-α-AP derivative in a mixed solvent of methanol, hydrochloric acid and water, and thereafter introducing an inert gas thereinto while stirring;

2) Suspending or dissolving an F-α-AP derivative in a mixed solvent of methanol, hydrochloric acid and water, and then stirring under reduced pressure;

3) Treating an F-α-AP derivative at 50°–80° C. for 10–90 minutes with a mixed solvent of methanol, water and 0.5–1.0 equivalents of hydrochloric acid per equivalent of the F-α-AP derivative. Cooling the mixture and then adding hydrochloric acid and introducing an inert gas into the mixture while stirring; or 4) Treating an F-α-AP derivative at 50°–80° C. for 10–90 minutes with a mixed solvent of methanol, water and 0.5–1.0 equivalents of hydrochloric acid per equivalent of the F-α-AP derivative. Cooling the mixture and then adding hydrochloric acid. The mixture is subsequently stirred under reduced pressure.

In all of these methods α-APM.HCl crystals precipitate over time, after which the crystals can be easily separated. Since the separability of the crystals is good, there are no problems relating to the separation thereof.

The concentration of F-α-APM and/or F-α-AP in the crystallization solution is suitably 0.2–1.5M/l, preferably 0.5–1.2M/l. In view of flowability the slurry concentration of α-APM.HCl is suitably 1.5M/1 or less.

Suitable inert gases useful in accordance with the present invention include any gases which are inert to the starting material and the product, and are not otherwise limited. Preferably, air, argon gas or nitrogen gas is used. The volume of gas to be used is not particularly limited. Further, the level of reduced pressure to be used according to the present invention is adequate even if very weak, for example, normally 30 Torr or greater is sufficient, preferably 30–80 Torr is used.

Suitable concentrations of the hydrochloric acid useful in accordance with the present invention include concentrations of at least 1 mole or more hydrochloric acid per mole of the F-α-AP derivative. Preferably, a concentration of 1.0–6.0 moles hydrochloric acid per liter of the total reaction solution is used. An excessively high concentration of HCl in the treatment solution is undesirable as cleavage of the peptide bonds or the ester bond can occur.

Suitable concentrations of methanol useful in accordance with the present invention include concentrations of 35–110 grams methanol per liter of the total reaction solution.

In general, when F-α-AP derivatives are converted to F-α-APM.HCl, if the concentration of the methanol is high, the production of α-L-aspartyl-L-phenylalanine methyl ester increases; whereas if it is low, the production of α-L-aspartyl-L-phenylalanine increases.

Suitably, the temperature of the treatment in accordance with the present invention is not particularly limited. However, if the temperature of treatment is overly high, the presence of impurities as well as the solubility of the α-APM increases. Preferably the temperature of the treatment is in the range of 0° C. to 40°

C. Also, the time of treatment is not particularly limited. Preferably the time of treatment is from 1–8 days.

Having generally described this invention, a further understanding can be obtained by reference to certain specific examples which are provided herein for purposes of illustration only and are not intended to be limiting unless otherwise specified.

EXAMPLE 1

To a mixed solution containing 15 ml methanol, 25 ml water, and 25 ml 35% aqueous hydrochloric acid was added 38.3 g F-α-APM. The mixture was stirred at 25° C. for 4 days while nitrogen gas was blown thereinto. The mixture was then stirred at 5° C. for 3 hours, after which the precipitated α-APM.HCl was filtered off. The amount of α-APM contained in the crystals was 29.4 g representing a yield of 84.1% with respect to the initial amount of F-α-APM.

Comparison 1

38.3 g F-α-APM was subjected to the same reaction conditions as in Example 1, except nitrogen gas was not introduced into the reaction mixture. The yield of obtained α-APM.HCl was 79.1% with respect to the initial amount of F-α-APM.

EXAMPLE 2

To a suspension of 21.5 g N-formyl-L-aspartic anhydride in 50 ml acetic acid was added 200 ml of a solution of 25.5 g L-phenylalanine methyl ester in toluene at room temperature over a period of 30 minutes. According to HPLC analysis, 38.1 g F-α-APM was produced in the reaction solution. The reaction solution was concentrated under reduced pressure while pouring 500 ml of toluene thereinto. Roughly 90% of the acetic acid was distilled off. Following this, 38 ml water was added and the solution was heated to 60° C. and stirred for 15 minutes. After which, the toluene layer and the aqueous layer were separated. To the obtained aqueous layer were added 13 ml methanol and 61 ml 35% aqueous hydrochloric acid. The mixture was stirred at 30° C. for 1 day, and additionally at 20° C. for 3 days while introducing air thereinto. After stirring the solution at 5° C. for 3 hours, the precipitated α-APM.HCl crystals were filtered off. The amount of α-APM contained in the crystals was 27.5 g representing a yield of 79.2% with respect to the initial amount of F-α-APM.

Comparison 2

21.5 g N-formyl-L-aspartic anhydride was subjected to the same reaction conditions as in Example 2, except air was not introduced into the reaction mixture. The yield of the obtained α-APM.HCl was 72.1% with respect to the initial amount of F-α-APM.

EXAMPLE 3

To a suspension of 21.5 g N-formyl-L-aspartic anhydride in 50 ml acetic acid was added 200 ml of a solution of 25.5 g L-phenylalanine methyl ester in toluene at room temperature over a period of 30 minutes. According to HPLC analysis, 38.1 g F-α-APM was produced in the reaction solution. The reaction solution was concentrated under reduced pressure while pouring 500 ml toluene thereinto. Roughly 90% of the acetic acid was distilled off. Following this, 38 ml water was added to the solution and heated to 60° C. The solution was then stirred for 15 minutes after which the toluene layer and the aqueous layer were separated. To the obtained aqueous layer were added 13 ml methanol and 13 ml 35% aqueous hydrochloric acid. The mixture was heated at 60° C. for 20 minutes and then cooled, after which 48 ml hydrochloric acid was further added thereto and the mixture was stirred at 20° C. for 3 days under a reduced pressure of 100 Torr. The mixture was stirred at 5° C. for 3 hours, after which the precipitated α-APM.HCl crystals were filtered off. The content of α-APM in the crystals was 28.8 g representing a yield of 82.9% with respect to F-α-APM to the initial amount.

Comparison 3

21.5 g N-formyl-L-aspartic anhydride was subjected to the same reaction conditions as in Example 3, except the reaction was not performed under reduced pressure. The yield of the obtained α-APM.HCl was 76.2% with respect to the initial amount of F-α-APM.

EXAMPLE 4

To a suspension of 34.4 g N-formyl-L-aspartic anhydride in a mixed solvent of 152 ml acetic acid and 50 ml methyl acetate was added 39.7 g L-phenylalanine at room temperature. The mixture was stirred at room temperature for 5 hours. According to HPLC analysis, 54.0 g of F-α-AP was produced. The reaction solution was concentrated under reduced pressure and 120 ml of the solvent was distilled off, after which 59 ml methanol, 30 ml 35% aqueous hydrochloric acid, and 20 ml water were added thereto and the mixture was heated at 60° C. for 30 minutes. The reaction solution was then cooled to 20° C. and 32 ml 35% aqueous hydrochloric acid was added thereto. The solution was stirred at 25° C. for 5 days while blowing in nitrogen gas. After stirring at 5° C. for 3 hours, the precipitated α-APM.HCl crystals were filtered off. The content of α-APM in the crystals was 40.3 g representing a 78.2% yield with respect to the initial amount of F-α-AP.

Comparison 4

34.4 g N-formyl-L-aspartic anhydride was subjected to the same reaction conditions as in Example 4, except nitrogen gas was not blown into the reaction mixture. The yield of the obtained α-APM.HCl was 73.4% with respect to the initial amount of F-α-AP.

EXAMPLE 5

To a mixed solvent of 50 ml 35% aqueous hydrochloric acid, 30 ml water and 20 ml methanol was added 55.0 g F-α-AP. The mixture was stirred at 25° C. for 6 days while blowing in air. After stirring at 5° C. for 3 hours, the precipitated α-APM.HCl crystals were filtered off. The content of α-APM in the crystals was 39.8 g representing a 76.0% yield with respect to the initial amount of F-α-AP.

Comparison 5

55.0 g F-α-AP were subjected to the same reaction conditions as in Example 5, except air was not blown into the reaction mixture. The yield of the obtained α-APM.HCl was 71.3% with respect to F-α-AP.

EXAMPLE 6

Two 3 liter jacketed separable flasks and one 2 liter four-necked flask were set up as shown in FIG. 1. (Explanation of Symbols: M Motor; 1 Inlet for mixed solution comprising an aqueous solution of F-APM+methanol; 2 Inlet for 35% aqueous hydrochloric acid; 3 Port through which slurry is drawn from first tank; 4, 7

Slurry pumps; 5 Inlet for slurry received from first tank; 6 Port through which slurry is drawn from second tank; 8 Inlet for slurry received from second tank; 9 Inlet ports for nitrogen gas.) 1 liter 3.5N hydrochloric acid and 100 g α-APM-HCl were added to the first tank to prepare an initial slurry which was then kept at 30° C. Into this first tank, a mixed solution of 1000 ml of an aqueous solution containing F-α-APM (F-α-APM: 530 g; F-β-APM: 98 g; AcOH: 60 g) prepared according to the same method as in Example 3 and 243 ml methanol were continuously fed over a period of 24 hours. Meanwhile, 645 ml of 35% aqueous hydrochloric acid was continuously fed into the first tank over a period of 24 hours, and the solution was thoroughly mixed by stirring.

After the course of one day, the amount of the slurry was 3 liters. While the mixed solution of 1000 ml of the aqueous solution containing F-α-APM and 243 ml methanol and 645 ml 35% aqueous hydrochloric acid were continuously fed each day, the slurry was continuously drawn from the first tank to the second tank at a rate of 1.9 l/day using a laboratory slurry pump, and after the slurry in the second tank reached a volume of 3.0 liters, a pump was used to draw it to the third tank in order to maintain that volume. The second and third tanks were kept at 20° C. and, as shown in FIG. 1, nitrogen gas was continuously blown into the first and second tanks. The third tank was replaced every day, and the collected slurry was further crystallized at 20° C. for 34.7 hours, after which it was cooled at 5° C. and then separated using a centrifuge.

The residence times in each of the tanks were 37.4 hours in the first tank, 39.5 hours in the second tank, and 46.7 hours in the third tank. This continuous crystallization was continued for 7 days. When the slurry obtained on the seventh day was separated, the amount of α-APM.HCl was 538 g and contained 390 g of α-APM (yield=76.1% with respect to the initial amount of F-α-APM which was 530 g).

Comparison 1

The same procedure as in Example 6 was followed, but without blowing nitrogen gas into the first and second tanks. The amount of separated crystals of α-APM-HCl obtained on the seventh day was 474 g and contained 311 g of α-APM (yield=64.5% with respect to the initial amount of F-α-APM).

What is claimed as new and desired to be secured by Letters Patent of the United States is:

1. A method for producing α-L-aspartyl-L-phenylalanine methyl ester hydrochloride which comprises treating an N-formyl-α-L-aspartyl-L-phenylalanine derivative with a mixed solvent of methanol, hydrochloric acid and water wherein said treatment is effected under reduced pressure.

2. The method according to claim 1, wherein said N-formyl-α-L-aspartyl-L-phenylalanine derivative is N-formyl-α-L-aspartyl-L-phenylalanine methyl ester.

3. The method according to claim 1, wherein said N-formyl-α-L-aspartyl-L-phenylalanine derivative is N-formyl-α-L-aspartyl-L-phenylalanine.

4. The method according to claim 2, wherein said N-formyl-α-L-aspartyl-L-phenylalanine methyl ester was produced in an organic solvent containing acetic acid.

5. The method according to claim 3, wherein said N-formyl-α-L-aspartyl-L-phenylalanine was produced in an organic solvent containing acetic acid.

6. The method according to claim 1, wherein said hydrochloric acid is added in portions during said treatment.

7. The method according to claim 1, wherein at least one mole or more of hydrochloric acid is present per mole of said F-α-AP derivative.

8. The method according to claim 7, wherein 1.0–6.0 moles of hydrochloric acid are present per liter of the total reaction solution.

9. The method according to claim 1, wherein 35–110 grams of methanol are present per liter of the total reaction solution.

* * * * *